United States Patent
Wessel

[11] 4,094,186
[45] June 13, 1978

[54] MIXTURE CONTROL MONITOR APPARATUS

[75] Inventor: Wolf Wessel, Oberriexingen, Germany

[73] Assignee: Robert Bosch GmbH, Stuttgart, Germany

[21] Appl. No.: 772,151

[22] Filed: Feb. 25, 1977

[30] Foreign Application Priority Data

Feb. 28, 1976 Germany .................. 2608245

[51] Int. Cl.² .............. G01N 31/00; F02M 7/00
[52] U.S. Cl. .............................. 73/1 G; 73/23; 60/277
[58] Field of Search .............. 73/1 G, 23, 27 R; 23/232 E, 254 E; 340/237 R; 60/277

[56] References Cited

U.S. PATENT DOCUMENTS

| | | | |
|---|---|---|---|
| 3,738,341 | 6/1973 | Loos | 73/23 |
| 3,851,469 | 12/1974 | Eichler et al. | 60/277 |
| 3,948,081 | 4/1976 | Wessel et al. | 73/23 |
| 4,024,707 | 5/1977 | Schmidt et al. | 60/277 |
| 4,024,850 | 5/1977 | Peter et al. | 60/277 |

*Primary Examiner*—Richard C. Queisser
*Assistant Examiner*—Stephen A. Kreitman
*Attorney, Agent, or Firm*—Edwin E. Greigg

[57] ABSTRACT

The mixture control system of an internal combustion engine which employs an exhaust gas oxygen sensor is provided with circuitry which subjects the output signal from the sensor to comparison with established threshold values to determine the operational readiness of the sensor. When the amplitude of the sensor signal is sufficiently high, indicating proper operational temperature of the sensor, the test signal is turned off and the monitoring is taken over by a circuit which looks for regular alternation of the sensor signal at a sufficiently rapid rate. When the sensor signal is found inadequate for any reason, the closed loop control system is disengaged and the mixture control is provided on the basis of an average sensor voltage supplied by the circuit.

10 Claims, 3 Drawing Figures

MIXTURE CONTROL MONITOR APPARATUS

BACKGROUND OF THE INVENTION

The invention relates to a method and an apparatus for monitoring the operational readiness of an oxygen sensor located in the exhaust gas system of the engine and responsible for generating signals for a mixture controller of the engine.

It is known to provide fuel-air mixture controllers for internal combustion engines in order to obtain exhaust gases free from toxic components. These controllers receive their signals from an oxygen sensor located in the exhaust gas system of the engine. This type of control is usually superimposed on a preliminary, coarse, forward control which determines the basic fuel-air mixture. A prerequisite for the satisfactory functioning of such a control system is the correct operation of the transducer, i.e., the oxygen sensor. Oxygen sensors which work on the principle of ion conduction through a solid electrolyte respond to a difference in the partial pressure of oxygen and generate a voltage signal according to the partial pressure of oxygen within the exhaust gas. This voltage signal undergoes an abrupt shift when the oxygen content in the exhaust gas makes a transition from an excess amount to a shortage, i.e., when the air factor $\lambda$ crosses the value $\lambda = 1$. A clear output signal is obtained, however, only when the oxygen sensor has reached a certain minimum operational temperature. When the sensor is too cold, the internal resistance of the sensor is too large to generate a sufficiently large output signal and, in particular, to provide a sufficiently clear potential shift. For this reason, when such sensors are normally heated to the operational temperature by the exhaust gases of the engine, it is necessary to provide a preliminary mixture adjustment which is supplanted by closed-loop mixture control based on the oxygen sensor output signal after the latter reaches its normal operational temperature.

In some operational states of the engine, the oxygen temperature may drop below its optimum value even when the engine is running. At any time, a defect in the sensor itself may cause suppression of the signal. If no precautions were taken to account for these malfunctions, they would lead to extremely erroneous adjustments of the fuel-air mixture. Furthermore, the mixture adjustment provided during the warm-up phase of the engine is not usually optimized with respect to the exhaust gas conditions so that a monitoring system for checking the operational readiness of the oxygen sensor is required.

In a known monitoring system of this kind, the alternating voltage signals coming from the oxygen sensor, the frequency of which depends on the manner of operation of the engine, are fed to a threshold switch that holds a switch in a first position as long as the period of sensor alternations is shorter than the time constant of the switch. In the opposite case, the switch is brought into its second position after the expiration of the time constant. The switch is then used to change the fuel-air mixture and/or to energize a warning signal.

The known apparatus just described has the inherent disadvantage as to be capable of indicating only the complete failure of the sensor if the latter fails to provide a signal of alternating magnitude due to a defect or due to lower than adequate operating temperatures.

OBJECT AND SUMMARY OF THE INVENTION

It is a principal object of the invention to overcome the above-mentioned disadvantages and to provide a monitoring system for an oxygen sensor which is capable not only of indicating complete failure but also to reliably indicate any reduction in the operational readiness of the oxygen sensor. It is a further object of the invention to provide a monitoring system which recognizes cases of reduced operational readiness of the sensor and switches the normal control system based on the sensor signal to a forward control method. Yet another object of the invention is to permit the controller to be re-engaged just as soon as the oxygen sensor reaches a sufficiently large voltage signal for reliable operation.

These and other objects are attained, according to the invention, by applying to the sensor a test voltage having a constant average value equal to the average value of the normally generated sensor voltage. The resultant total voltage at the output of the sensor is used as a control variable to indicate the operational readiness of the sensor and is fed to two comparators for comparison, respectively, with an upper and a lower set point value of a minimum permissible output voltage for the sensor. Depending on the result of the comparison, the output signal of the comparators switches a timing member and causes control to be shifted from a mixture control system to a mixture adjustment system and vice versa.

According to the method of the present invention, two values of voltage corresponding, respectively, to the minimum and maximum voltage normally generated by a correctly functioning sensor, are determined. As soon as the output voltage of the sensor exceeds these threshold values as it is being heated, the comparator circuits recognize that fact and cause a timing member to turn off the forward mixture adjustment but cause it to be re-inserted into the system if there is not present a sensor signal alternating with sufficient rapidity.

In a further feature of the method of the apparatus, the timing member turns the test voltage on and off at the same time as it switches the mixture adjustment device on and off. In this manner, the oxygen sensor is not loaded with the test voltage as long as the sensor generates a sequence of voltage signals of alternating magnitude. When the test voltage is absent, the operational readiness of the sensor is instead monitored by checking the rapidity of the signal alternations per unit time by means of a timing circuit which causes the re-connection of the mixture adjustment system and of the test voltage when the sensor function is inadequate.

A preferred exemplary apparatus for practicing the method of the invention provides means for applying a positive average test voltage to the oxygen sensor via a resistor and a bridge circuit having two threshold switches, respectively associated with an upper and lower threshold, to which is applied the potential at the junction between the sensor and the resistor. The output of the threshold switches is fed through a diode to a timing element which in turn actuates a switch that switches the output of the mixture controller to an average potential which is used to adjust the mixture and which also causes one of the threshold switches to be turned off.

In order to produce the test voltages there is provided, according to the invention, a voltage-stabilized voltage divider which may be disconnected from its power source depending on the state of the timing element. In this manner, any load voltages are disconnected from the sensor during the period of time in which it is used to control the mixture.

Another embodiment of the invention is based on an apparatus for controlling the mixture of an engine which includes a comparator acting as a threshold switch which is part of a bridge circuit and compares a voltage from the oxygen sensor with a set point value and includes a control amplifier with integral behavior, the output of which is coupled to a final control element that adjusts the mixture. According to the invention, the threshold switch is also used as the first threshold switch of the monitor circuit and the second threshold switch of the monitor is connected in parallel and is also connected with a voltage divider which provides the second set point value. In this manner, the threshold switch required in any case for normal operation of the controller, as well as the bridge circuit, are used for the operation of the monitoring system.

The invention will be better understood as well as further objects and advantages thereof become more apparent from the ensuing detailed description of a preferred embodiment of the invention taken in conjunction with the drawing.

DESCRIPTION OF THE PREFERRED EMBODIMENT

Figure 1:
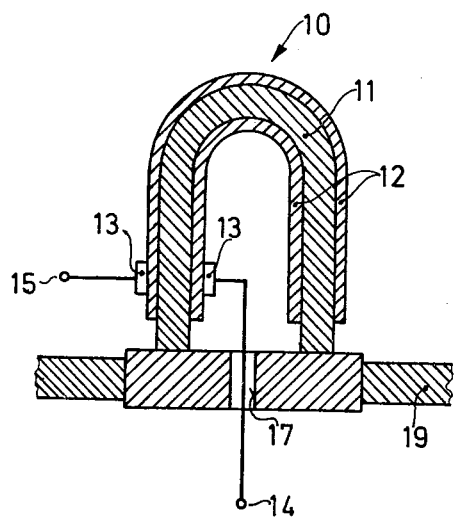
FIG. 1 is a schematic representation of an oxygen sensor used in the apparatus of the invention.

The oxygen sensor 10 in FIG. 1 is a tube 11 closed at one end and made from a solid electrolyte. Both surfaces of the little tube 11 are covered with a layer of microporous platinum 12 each provided with electrical contacts 13 and connecting wires 14 and 15, respectively. The tube 11 is inserted into the bore 17 of a socket 16 which is tightly inserted in the wall of an exhaust pipe 19 of the internal combustion engine.

Figure 2:
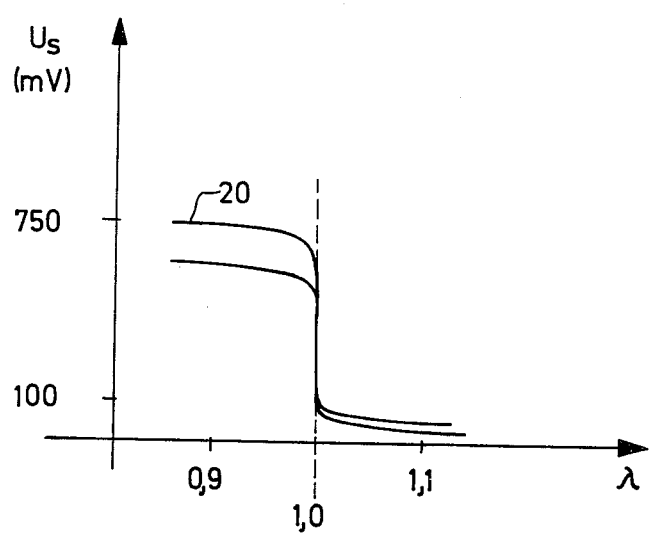
FIG. 2 is a diagram illustrating the output voltage of the oxygen sensor as a function of the air factor $\lambda$ at different temperatures.

Oxygen contained in the ambient atmosphere may reach the platinum layer 12 through the central bore 17. The outer layer of platinum which extends into the exhaust pipe 19 is exposed to the oxygen in the exhaust gas. The solid electrolyte may be, for example, zirconium dioxide which becomes conducting for oxygen ions at elevated temperatures such as prevail in the exhaust gas stream. When the partial pressure of oxygen within the exhaust gas is different from that in the ambient air, a potential difference is generated across the two contacts 13, the behavior of which as a function of the air factor $\lambda$ is illustrated by a curve 20 in FIG. 2. The potential difference between the two contacts 13 is a logarithmic function of the quotient of the oxygen pressures on the two sides of the tube 10. For this reason, the output voltage of the oxygen sensor abruptly changes when the air factor $\lambda$ crosses the value 1.0. When the air factor values are smaller than 1, the output voltage is relatively high whereas, when the air factor is greater than 1, the maximum output voltage between the contacts 13 goes to a relatively low value. Inasmuch as the internal resistance of the solid electrolyte is very highly dependent on temperature, the maximum output voltage of a sensor which is warming up, for example when the engine itself is warming up, changes continuously. If the sensor has been sufficiently warmed up, and the air factor is less than 1, corresponding to a rich operational mixture, the sensor may generate a voltage exceeding 750 millivolt. If the air factor $\lambda > 1$ corresponding to a lean mixture, the open circuit voltage may be less than 100 millivolt. When the sensor is cold, the maximum output voltage is lower as is also illustrated in FIG. 2.

Figure 3:
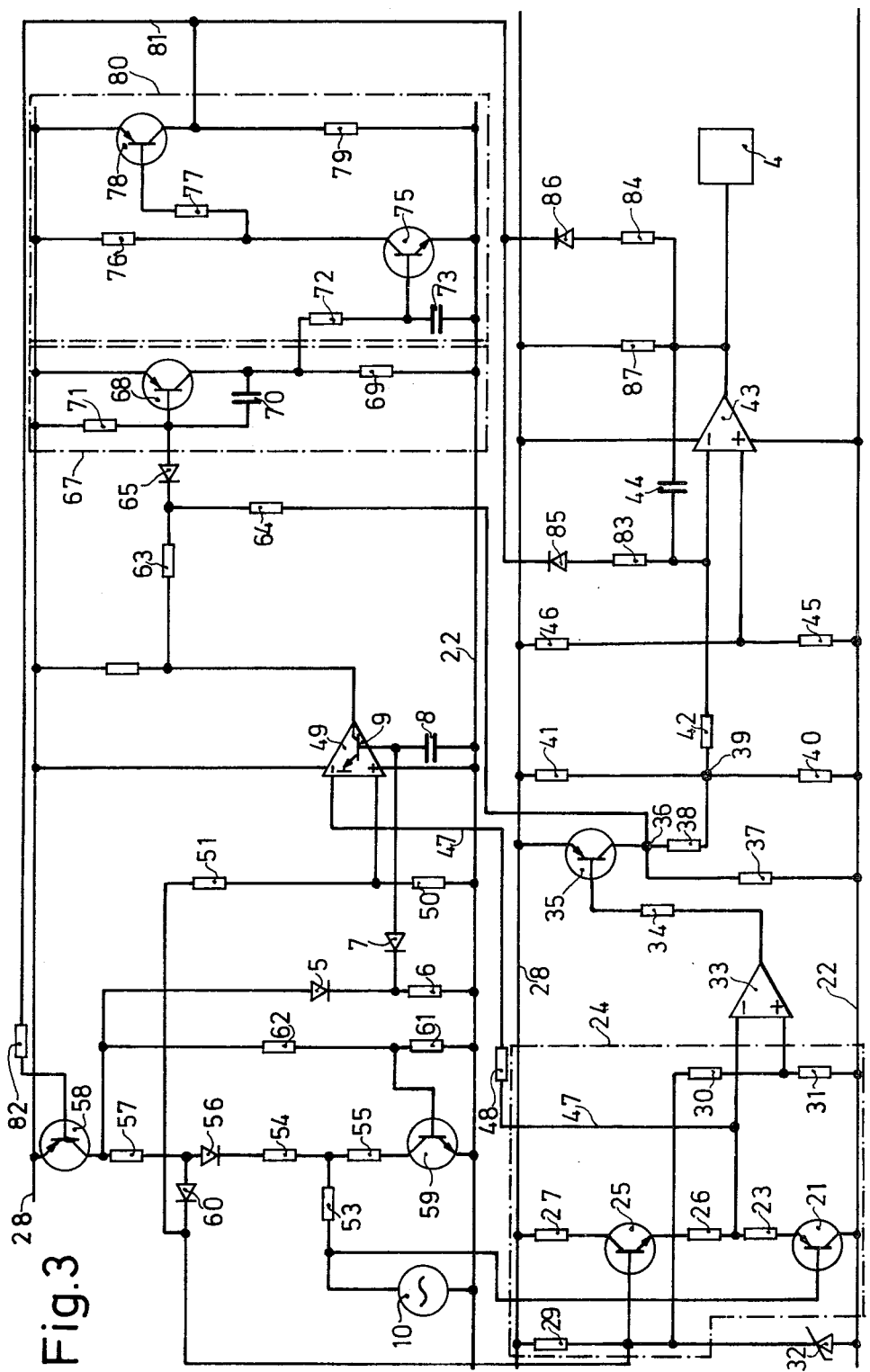
FIG. 3 is a schematic diagram of an exemplary embodiment of an apparatus according to the invention.

FIG. 3 is a schematic diagram of the circuitry associated with the apparatus according to the invention. The oxygen sensor 10 is indicated schematically as a voltage source, the output of which is fed to the base of a PNP transistor 21 lying in a first branch of a bridge circuit 24. The transistor 21 is connected as an emitter follower and its collector is connected to a common supply line 22. The emitter of the transistor 21 is connected to a resistor 23. The collector-emitter path of the transistor 21 and the series resistor 23 constitute the first branch of the bridge circuit 24. The second branch of the bridge circuit 24 is formed by the series connection of the collector-emitter path of a transistor 25 and a resistor 26. The collector of the resistor 25 is connected through a protective resistance 27 to a common positive supply line 28. A voltage divider consisting of series resistors 29, 30 and 31 is connected between the two supply lines 28 and 22 and serves to bias the base of the transistor 25. Connected in parallel with resistors 30 and 31 is a Zener diode 32 blocking the path to the supply line 22 for purposes of voltage stabilization. The resistors 30 and 31 constitute the third and fourth branches, respectively, of the bridge circuit 24. The base of the transistor 25 is connected to the junction of the resistors 29 and 30 and thus also receives a stabilized voltage.

The diagonal of the bridge circuit 24 is connected across the inputs of an operational amplifier 33, operating as a threshold switch. The inverting input of the operational amplifier 33 is connected to the junction of the resistor 26 and the emitter resistor 23 associated with the transistor 21. The non-inverting input of the operational amplifier is connected to the junction of resistors 30 and 31. The output of the operational amplifier 33 is connected through a resistor 34 with the base of a further PNP transistor 35 whose emitter is connected to the common positive supply line 28 and whose collector is connected with a junction point 36. The junction point 36 is further connected through a resistor 37 to the negative supply line 22. Still further, the junction point 36 is connected via a resistor 38 to the central tap 39 of a voltage divider consisting of two resistors 41 and 40 connected between the two supply lines 28 and 22. A resistor 42 is connected between the tap 39 and the inverting input of an operational amplifier 43 acting as control amplifier. A capacitor which imparts to the control amplifier integrating behavior is connected between the output of the amplifier and its inverting input. The output of the operational amplifier 43 is further connected with a final control element 4 which is part of the overall control system and alters the composition of the fuel-air mixture of the engine. The control element 4 is not described further because of the manifold possibilities of changing the fuel-air mixture with such a controller. In known manner, the non-inverting input of the operational amplifier is supplied with a reference voltage by means of a voltage divider consisting of resistors 45 and 46.

A line 47 is connected from the junction of resistors 26 and 23 via a resistor 48 to the inverting input of a further operational amplifier 49 serving as a threshold switch. The non-inverting input of the latter amplifier is supplied with a voltage by a voltage divider consisting of resistors 50 and 51 connected between the common supply line 22 on the one hand, and the junction between resistors 29 and 30 which carries a stabilized voltage. This voltage divider, together with the first and second branches of the bridge circuit 24, constitutes a second bridge circuit for controlling the operational amplifier 49 serving as the second threshold switch.

The oxygen sensor 10 is connected to the base of the transistor 21 and thereby influences the first branch of the bridge circuit 24. The sensor is supplied with a voltage derived by a voltage divider consisting of resistors 54 and 55 which passes through a series resistor 53. The voltage divider consisting of resistors 54 and 55 is connected through a diode 56 and a resistor 57 as well as a switch 58 to the positive supply line 28. The first switch 58 includes a PNP transistor whose collector-emitter path is connected between a resistor 57 and the positive supply line 28. The other side of the voltage divider is connected over the emitter-collector path of a second switch 59, illustrated here as an NPN transistor connected to the common supply line 22. The junction between the resistor 57 and the diode 56 is further connected through a diode 60 to the stabilized voltage supplied by the Zener diode 32. A voltage divider consisting of resistors 61 and 62 is connected between the collector of the transistor 58 and the line 22. The junction of resistors 61 and 62 is connected to the base of the transistor 59 which thereby remains conducting as long as the transistor 58 also conducts and maintains the connection to the supply line 28.

When the voltage supply to the base of the transistor 59 is interrupted, the second threshold switch is also interruptable. For this purpose, a line branches off from the collector of the first transistor 58 leading to the supply line 22 and contains a series-connected diode 5 with indicated polarity, followed by a resistor 6. Furthermore, the base of an NPN output transistor 9 within the second threshold switch 49 is connected through a diode 7 followed by a resistor 6 to ground and, connected parallel thereto, is a capacitor 8 also connected to ground.

The output of the second threshold switch 49 and the junction point 36 are connected via resistors 63 and 64, respectively, through a blocking diode 65 with a timing circuit 67. This timing circuit includes a known Miller integrator having a PNP transistor 68 whose emitter is connected to the positive supply line 28 and whose collector is connected through a resistor 69 to the line 22. A capacitor 70 is connected between the collector and the base of the transistor 68, thereby determining the time constant of the timing circuit. The base of the transistor 68 is further connected through a resistor 71 to the positive supply line 28 and through the previously mentioned diode 65 to the lower potential of the line 22 depending on the condition of the output of the second threshold switch 49.

Connected in parallel to the collector resistor 69 of the transistor 68 is a resistor 72 in series with a capacitor 73 connected to the negative line 22. The junction between the two latter components is connected to the base of an NPN transistor 75. The emitter of the latter transistor is connected to the line 22 while the collector is connected through a resistor 76 to the supply line 28. The collector of the transistor 75 is further connected through a series resistor 77 to the base of a further PNP transistor 78. The collector of the transistor 78 is connected through a collector resistor 79 to the supply line 22. The two transistors 75 and 78 serve as a switch 80 by means of which the base of the first transistor 58 receives a positive or negative potential depending on the condition of the transistor 78 as transmitted via a line 81 connected to the collector of the transistor 78.

The line 81 is further connected to the inverting input of the control amplifier 43 through a blocking diode 85 and a resistor 83 and is also connected to its output via a blocking diode 86 and a resistor 84. The output of the control amplifier 43 is further connected in usual manner via a resistor 87 to the positive supply potential of the line 28.

The manner of operation of the control and monitoring system illustrated schematically in FIG. 3 is as follows. Beginning with the condition in which the first switch, i.e., the transistor 58, conducts, the base of the second transistor 59 receives a positive voltage causing it to conduct as well. In that case, the voltage divider consisting of the resistors 54 and 55 is supplied with a voltage stabilized by the Zener diode 32. Therefore, the oxygen sensor 10 receives via the resistor 53 a voltage which is so adjusted as to constitute an average value between the minimum and maximum voltages normally supplied by the oxygen sensor in operation. For example, if the maximum voltage supplied by the oxygen sensor during normal operation is approximately 750 millivolt and if its minimum voltage is approximately 100 millivolt, the average voltage referred to would be approximately 425 millivolt. Depending on the magnitude of the internal resistance of the oxygen sensor and the resistance of the resistor 53, the output of the sensor will carry a voltage which, depending on the instantaneous value of the air factor $\lambda$, will be between 425 and 750 millivolt or between 425 and 100 millivolt. The voltages actually produced will be transmitted through the resistor 21 to the bridge circuit 24. The voltage thereby occurring between the resistors 23 and 26 of the first and second branch which is fed to the inverting input of the first threshold switch 33 is compared with the threshold value formed by the resistors 30 and 31 and applied to the non-inverting input of the switch 33. At the same time, the voltage between the first and second branches is also fed to the inverting input of the second threshold switch 49, the non-inverting input of which receives an adjustable threshold potential via the resistors 51 and 50. Inasmuch as the voltage applied to the various branches of the bridge circuits is stabilized, the threshold values of the first and second threshold switches can be kept constant. The threshold switch 49 is set to an upper value corresponding to an average resulting voltage at the output of the sensor of approximately 500 millivolt. The first threshold switch 33 is set for a threshold corresponding to approximately 350 millivolt.

As soon as the sensor arrives at an operational state, its output voltage would exceed the upper threshold of the switch 49 as soon as the mixture becomes such as to exhibit an air factor smaller than $\lambda = 1$. The output of the threshold switch 49 then is negative, i.e., equal to the potential of the line 22. Accordingly, the base of the transistor 68 and the capacitor 70 of the Miller integrator 67 are also placed at negative potential. As soon as the transistor 68 conducts, and after a short time in which the capacitor 73 of the RC member 73, 72 is charged, the base of the transistor 75 becomes positive, thereby causing it to conduct. At the same instant, the base of the transistor 78 is made negative via the resistor 77, thereby causing that transistor to conduct and to apply the potential of the supply line 28 to the control line. Accordingly, the first transistor 58 blocks, followed by the second transistor 59, the base of which is separated from the supply line 28 by the first cut-off switch 58. From this moment on, the voltage divider consisting of resistors 54 and 55 is without current so that no further voltage is applied to the oxygen sensor. The same process takes place when the output voltage of the oxygen sensor falls below the 350 millivolt threshold while the first and second transistors 58 and 59 are conducting. In that case, the output of the first threshold switch 33 is positive and blocks the transistor 35. Consequently, the connection of the point 36 with the positive supply line 28 is interrupted and the diode 65 is brought to the negative potential of the line 22 through the resistors 64 and 37. Thus the transistor 68 of the Miller integrator also conducts, followed by the transistor 75 and the transistor 78 so that the first transistor 58 is blocked again and the voltage divider 54, 55 is without potential. At the same time, the cathode of the diode 7 which previously had been at the positive potential of the diode 5, is brought to the negative potential of the line 22 through the resistor 6, thereby applying a negative blocking potential to the output transistor 9 of the second threshold switch.

In that situation, the conducting transistor 35 passes positive potential to the diode 65 so that, after the expiration of the time determined by the resistor 71 and the capacitance of the capacitor 70, the transistor 68 is blocked again unless, during that time, a negative potential has reached the diode 65. On the other hand, when the sensor initially indicates an output voltage corresponding to a rich mixture, the control system so adjusts the composition as to be changed in the direction of a lean mixture so as to obtain an air factor of $\lambda = 1$. This occurs until after the output voltage has passed its step change, and attains a value lying below the lower threshold of the first threshold switch 33. The output of that switch then is positive, which blocks the transistor 35 and applies a negative signal to the diode 65. Therefore, if the signal comes in time, the transistor 68 remains conducting and the test voltage as well as the second threshold switch 49 remain turned off. This condition persists as long as the signal supplied by the threshold switch 33 alternates from positive to negative sufficiently often. If the oxygen sensor is not providing such a signal due, to its being in a non-operational condition, the transistor 68 is blocked and the first and second transistors 58 and 59 are sequentially switched on. This causes the monitoring system for the oxygen sensor to be re-engaged and, at the same time, causes the control system to be turned off and a simple mixture adjustment to be switched on.

As long as the oxygen sensor is operational and does generate a control signal which alternates sufficiently rapidly, the inverting input of the control amplifier 43 receives an alternating voltage which it uses to integrate and supply to the control element 4. This will be the case as long as the cathodes of the diodes 85 and 86 are lying at the positive potential of the control line 81, i.e., as long as the test voltage coming from the voltage divider 54, 55 is turned off. If however the control line 81 is at negative potential, the resistors 87 and 84 act as a voltage divider which, together with the effect of the coupling of line 81 through the diode 85 and the resistor 83 to the inverting input of the amplifier, causes the latter to put out an average potential for setting the final control element 4.

As long as neither the upper or lower threshold is crossed, the mixture of the engine is set by an adjustment which corresponds to the fixed average output voltage of the control amplifier. However, as the oxygen sensor is heated, the threshold value is eventually exceeded and the control line 81 becomes positive with the result that the test voltage is turned off and the normal function of the control amplifier is initiated by the first threshold switch.

A principal advantage of the invention is that the closed control of the mixture begins automatically after the vehicle has started as soon as the sensor has reached its operational temperature. Furthermore, if the sensor fails and if no regularly alternating signal occurs, the overall control of the mixture is switched over to a mixture adjustment which follows an average air factor $\lambda$ and maintains the operational capability of the vehicle powered by the engine.

The foregoing relates to a preferred exemplary embodiment of the invention, it being understood that other embodiments and variants are possible within the spirit and scope of the invention, the latter being defined by the appended claims.

What is claimed is:

1. A method for monitoring the operation of an oxygen sensor in a fuel control system comprising the steps of:
   applying a test voltage to said oxygen sensor;
   applying the output voltage from said sensor to at least two voltage comparator circuits and comparing it with set point values associated, respectively, with the upper and lower nominal values of said sensor in normal operation thereof;
   applying the output signal from said comparator circuits to a timing circuit for enabling a switch which changes the operation of the fuel injection system from closed loop control based on oxygen sensor signals to open loop forward control based on signals from transducers of engine variables.

2. A method as defined in claim 1, wherein said switch simultaneously cuts off said closed loop mixture control, said test voltage and one of said two comparator circuits.

3. An apparatus for monitoring the operation of an oxygen sensor in a fuel control system comprising:
   an oxygen sensor, located in the exhaust system of an internal combustion engine;
   circuit means for applying a test voltage of predetermined magnitude to the terminal of said oxygen sensor;
   a bridge circuit containing a first and a second threshold switch, each connected to receive the output voltage from said oxygen sensor and for outputting a control signal related to the difference between the relative magnitude of said output voltage and lower and upper nominal values of said output voltage in normal sensor operation;
   a timing circuit, connected to receive the outputs from said first and second threshold switches;
   a voltage source, connected to be activated by said timing circuit, for generating a substitute average datum for use in the fuel control system;
   switching means for switching between said control signal and said average datum; and a final control element, subject to said datum from said control system for providing a fuel-air mixture to said internal combustion engine.

4. An apparatus as defined by claim 3, wherein said circuit means for applying a test voltage includes a voltage stabilized voltage divider connected between respective power supply lines of said apparatus and including means for electrically disconnecting said voltage divider from said power supply lines under the influence of an inverter circuit triggered by said timing circuit.

5. An apparatus as defined by claim 4, wherein said means for disconnecting said voltage divider from said power supply lines includes a first transistor controlled by said inverter and a second transistor controlled by said voltage divider itself connected between said two transistors.

6. An apparatus as defined by claim 5, wherein said timing circuit is a Miller integrator the output of which is connected via an RC time delay member to the base of a third transistor serving as inverter for applying the voltage from one or the other voltage supply line to the base of said first transistor.

7. An apparatus as defined by claim 6, wherein said bridge circuit includes a comparator for comparing the voltage from said oxygen sensor with a nominal value and wherein said apparatus further comprises a control amplifier with integral characteristics, the output of which is coupled to said final control element, and wherein said comparator also serves as said first threshold switch of said monitoring apparatus and wherein said second threshold switch of said monitoring apparatus is connected in parallel with said first threshold switch and receives a set point value from a voltage divider.

8. An apparatus as defined by claim 7, wherein said control amplifier includes an operational amplifier having an integrating capacitor connected between its output and its inverting input, and wherein the output and the inverting input of said operational amplifier are connectd through resistors and diodes with the base of said first transistor for uncoupling said circuit means for applying a test voltage from one of the supply lines of the apparatus.

9. An apparatus as defined by claim 8, wherein said second threshold switch includes an output transistor connected through a diode and a resistor to the negative supply line of the apparatus as long as a connection is established between the positive supply line of said apparatus via said first transistor and a diode to said resistor.

10. An apparatus as defined by claim 9, including a further transistor connected between said first threshold switch and the inverting input of said control amplifier, the base of said further transistor being coupled to the output of said first threshold switch, and its collector being connected via a diode to the input of said timing circuit, said transistor having a collector resistor and connected in parallel thereto a further resistor connected to the central tap of a voltage divider supplying voltage to the inverting input of said control amplifier.

* * * * *